United States Patent [19]

Wolf et al.

[11] Patent Number: 5,707,869
[45] Date of Patent: Jan. 13, 1998

[54] COMPARTMENTALIZED MULTIPLE WELL TISSUE CULTURE PLATE

[76] Inventors: Martin L. Wolf, 1280 Keston St., St. Paul, Minn. 55108; John R. Wilson, 173 Windsor La., New Brighton, Minn. 55112

[21] Appl. No.: 413,334

[22] Filed: Mar. 30, 1995

Related U.S. Application Data

[63] Continuation-in-part of Ser. No. 268,073, Jun. 28, 1994, abandoned.

[51] Int. Cl.$^6$ .................... C12N 5/00; C12M 3/06
[52] U.S. Cl. .............. 435/401; 435/297.5; 435/304.2; 435/304.3
[58] Field of Search .............. 435/240.1, 240.2, 435/240.23, 240.241, 240.25, 288.3, 288.4, 288.5, 297.5, 297.1, 305.1–305.4, 304.1–304.3, 288.1, 288.2, 399, 401, 402

[56] References Cited

U.S. PATENT DOCUMENTS

| | | |
|---|---|---|
| 3,597,326 | 8/1971 | Liner . |
| 4,012,288 | 3/1977 | Lyman et al. . |
| 4,296,205 | 10/1981 | Verma . |
| 4,599,315 | 7/1986 | Terasaki et al. . |
| 4,661,455 | 4/1987 | Hubbard .................... 435/285 |
| 4,748,124 | 5/1988 | Vogler . |
| 4,839,292 | 6/1989 | Cremonese .................... 435/311 |
| 4,937,196 | 6/1990 | Wrasidlo et al. .................... 435/284 |
| 5,068,195 | 11/1991 | Howell et al. .................... 435/284 |
| 5,141,718 | 8/1992 | Clark .................... 422/99 |
| 5,153,131 | 10/1992 | Wolf et al. .................... 435/284 |
| 5,225,346 | 7/1993 | Matsumiya et al. .................... 435/284 |

FOREIGN PATENT DOCUMENTS 0155237   9/1985   European Pat. Off. .

OTHER PUBLICATIONS

Gibco BRL Catalogue & Reference Guide (1992) pp.7–9 and 78.

"Diffusion in Tissue Cultures on Gas–permeable and Impermeable Support", Mona D. Jensen, J. theor. Biol. (1976) 56, 443–458.

"Factors affecting cell growth and monoclonal antibody production in stirred reactors", S. Reuveny, et al., Journal of Immunological Methods, 86 (1986)53–59.

Original Articles, The Lancel, Dec. 16, 1967, pp. 1279–1281.

*Primary Examiner*—William H. Beisner
*Attorney, Agent, or Firm*—Sprung Kramer Schaefer & Briscoe

[57] ABSTRACT

A cell culture device comprising a container having a plurality of wells. Each well includes a cell culture compartment defined by a lower gas permeable film and an upper sheet selectively permeable to compounds of selected sizes. The device allows culture medium to reside between the upper sheet and the lower gas permeable film. A basal medium compartment is located above the upper sheet and allows basal medium to reside upon the upper sheet. Each compartment contains an access port. A gas film support below and in partial contact with the gas permeable film holds the gas permeable film in a substantially horizontal position so that suspension or adherent cells can distribute across the surface of the gas permeable film.

24 Claims, 9 Drawing Sheets

COMPARTMENTALIZED MULTIPLE WELL TISSUE CULTURE PLATE

This is a continuation-in-part of application Ser. No. 08/268,073, filed Jun. 28, 1994, now abandoned.

BACKGROUND—FIELD OF THE INVENTION

This invention relates to a device and a method for growing cells or tissue in vitro.

BACKGROUND—DESCRIPTION OF PRIOR ART

In vitro growth of mammalian cells is commonly conducted in static culture vessels such as multiple well tissue culture plates (U.S. Pat. No. 3,597,326 issued Aug. 3, 1971 and U.S. Pat. No. 4,012,288 issued Mar. 15, 1977) and Terisaki tissue culture plates (U.S. Pat. No. 4,599,315). In this type of culture, a portion of the cell culture medium is periodically removed from the bag and replaced as cells consume nutrients and produce waste products. This protocol leads to the disadvantages of limited cell density, limited cell secreted product concentration, and periodic shifts in nutrient concentration.

Marbrook used a dialysis membrane to separate cells and cell secreted products from the basal medium, allowing passive diffusion to meet the metabolic demands of the cells (Marbrook, J., "Primary Immune Response in Cultures of Spleen Cells", the Lancet, 2, 1279–1281 [1967]). In this device, an inner concentric chamber resides within an outer concentric chamber. The bottom of the inner chamber is comprised of a dialysis membrane which is submerged in basal medium contained in the outer chamber. Cells reside on the membrane receiving nutrients and delivering waste products. Continuous dialysis becomes limited as the membrane loses substrate transport capacity due to the cell mass that resides upon it. Thus, the ability to carry out long term culture is compromised.

Verma (U.S. Pat. No. 4,296,205 issued Oct. 20, 1981) teaches of the use of a tissue culture shelf placed in the cell culture compartment to keep cells from directly contacting and clogging the dialysis membrane. The tissue culture shelf has perforations to allow movement of nutrients to the cells. During the culture of suspension cells, the cells and cellular debris are capable of moving through the perforations and coming to rest upon the dialysis membrane, limiting continuous dialysis in long term culture. Also, the architectural structure of the shelf can lead to microenvironments as concentration gradients are unevenly distributed across the surface of the plate.

Vogler (U.S. Pat. No. 4,748,124 issued May 31, 1988) describes a cell culture compartment that is defined by a lower gas permeable, liquid impermeable sheet and an upper dialysis membrane. This configuration keeps the dialysis membrane from dogging as cells do not reside upon it, yet dialysis can become limited by other means. As with traditional multiple well tissue culture plates, the configuration of Vogler limits the ability to vary oxygen tension is limited relative to Marbrook and Verma. Furthermore, the surface chemistry of materials used to allow gas transfer are limited and in some cases can be undesirable for protein or cell contact. Finally, the teaching does not lead to high density cell culture relative to traditional static culture methods.

The architecture of Vogler can allow dialysis of the cell compartment to become limited. A major problem can arise as liquid evaporates from the growth chamber. Vapor transmission across gas permeable surfaces can be substantial and the loss of liquid will lead to termination of dialysis as liquid contact with the dialysis membrane ceases. Loss of dialysis will also result from off gassing of cell culture medium. Cell culture medium is typically stored at 4° Celsius. As the medium rises in temperature, the gas carrying capacity is reduced and gas bubbles rise and come in contact with the dialysis membrane.

The gas permeable, liquid impermeable sheet of the cell culture compartment limits options available for controlling pericellular pH and oxygen partial pressure. In the prior configurations of Marbrook and Verma, the oxygen tension could be varied by adjusting the liquid level of the cell culture compartment. The structure and method taught by Vogler require oxygen tension be varied by altering the ambient conditions of the atmosphere surrounding the device.

Oxygen tension is very important to cell viability and protein secretion (Reuveny et al., "Factors Affecting Cell Growth and Monoclonal Antibody Production in Stirred Reactors", Journal of Immunological Methods, 86, 53–59 [1986]). The gas permeability of commercially available liquid impermeable sheets and the impact upon pericellular pH and oxygen partial pressure is described in detail by Jenson et al. (Jenson M. D., Wallach D. F. H., and Sherwood P., "Diffusion in Tissue Cultures on Gas-permeable and Impermeable Supports", J. Theor. Biol. (1976) 56, 443–458). The oxygen demands of various cell types combined with the gas permeability of various gas permeable, liquid impermeable sheets will dictate a specific steady state pericellular pH and oxygen partial pressure for each combination. This means cell lines are subject to very limited pericellular conditions. Creating different pericellular conditions is achieved by altering the ambient conditions of the incubator in which the device resides. As a practical matter, this is difficult for researchers who maintain incubators at standard conditions for a wide variety of simultaneous uses.

Gas permeable, liquid impermeable sheets also limit the surface chemistry available for support of cells and protein structures. The proliferation and function of many cell types is strongly affected by the chemical nature of the surfaces they reside upon. The surface chemistry of liquid impermeable material is incompatible with many cell types and protein structures. Also, hydrophobic material which is often the basis for gas permeable, liquid impermeable films, can cause non-specific protein binding. This in turn can lead to depletion of soluble growth factors.

The architecture of Vogler also leads to limited cell density. The growth chamber will deform in shape due to the weight of liquid residing upon it and pressure of fluid expansion, leading to a sagging gas permeable sheet. This allows suspension cells to settle in the low point of the sheet. High localized cell densities at the low point of the sheet leads to excessive resistance to flux of nutrients and a localized reduction in cell viability. Furthermore, the cells are unable to expand to other areas of the gas permeable sheet.

It is accordingly an object of the present invention to provide a method and device in a multiple well tissue culture plate format for the long term culture of anchorage dependent cells and suspension cells at high density, simultaneously allowing variable oxygen tension, an even distribution of cells across the bottom of the culture compartment, uninterrupted dialysis, and a wide variety of surface chemistry options. Still further objects and advantages will become apparent from consideration of the ensuing description and drawings.

SUMMARY OF THE INVENTION

Many problems of the prior art are solved by a compartmentalized multiple well tissue culture plate constructed in accordance with this invention to allow cells to be cultured at high density over a long period of time.

Specifically, there is provided a plurality of cell culture compartments each including a lower gas permeable film and spaced vertically therefrom an upper sheet selectively permeable to compounds of selected sizes, means spacing said film from said sheet so as to allow a culture medium to reside between said upper sheet and said lower gas permeable film. There is a means defining a basal medium compartment to allow a basal medium to reside upon said upper sheet. There are access ports to each of said cell culture compartments and to said basal medium compartment. There exists a gas film support below and in partial contact with each of said gas permeable films whereby a major portion of each gas permeable film is held in a substantially horizontal position such that suspension cells can distribute across the horizontal portion of said gas permeable film and gas transfer into and out of said cell culture compartment is not substantially impaired.

According to another embodiment of the invention, the basal medium compartment is subdivided into a plurality of compartments. Each basal medium compartment is in communication with only one of the cell culture compartments by way of the upper membrane selectively permeable to a specific class of molecules and compounds. There exists one basal medium compartment for each cell culture compartment.

According to a further feature of the invention, the cell culture compartment volume can be varied during operation with out interrupting dialysis.

In accordance with a preferred embodiment the cell culture compartment also includes an upper sheet having a surface area at least one quarter of the surface of the lower gas permeable film, and the distance between a substantially horizontal portion of the lower gas permeable film and the upper sheet is less than 15 millimeters.

In accordance with another feature the oxygen control compartment is in communication with said basal medium and adapted by appropriate means to allow a selected volume of said basal medium to reside in the oxygen control compartment.

The lower cell culture compartment is configured such that it's bottom is comprised of a lower gas permeable film and is constrained in a horizontal and flat position. In this manner, suspension and adherent cells can spread out evenly upon the entire surface of the gas permeable film. The gas permeable film can be any biocompatible liquid permeable or impermeable, hydrophobic or hydrophilic, porous or non porous material which provides the appropriate pericellular environment and surface chemistry for a specific cell culture application.

The upper basal medium compartment and the lower cell culture compartment are configured to prevent pressurization due to temperature increase. The cell culture compartment is configured to prevent loss of dialysis due to evaporation or off-gassing, compensate for liquid flux from the basal medium reservoir, and allow high cell density cultures to be maintained over a long period of time.

According to a further feature of the invention, evaporative loss of cell culture medium can be controlled independent of ambient conditions by providing gaseous exchange of the cell culture compartment by way of the humidified gas of the upper basal medium compartment.

According to a further feature of the invention, oxygen tension within the cell culture compartment can be accurately controlled independent of ambient conditions by adding a third compartment that utilizes a variable level of liquid to alter oxygen tension.

With these structures, a method of culturing cells at high density becomes available. Also, a method of controlling oxygen tension surrounding cells becomes available by utilizing a liquid barrier to oxygen flux.

With the invention so stated, problems associated with the prior art are solved. Long term, high density, in vitro culture of both suspension and adherent cells is possible with simultaneous provisions for variable oxygen tension, controlled evaporation, long term maintenance of small cell compartment liquid volumes, and uninterrupted dialysis.

A BRIEF DESCRIPTION OF THE DRAWINGS

The invention will be further described with reference to the accompanying drawings wherein.

Figure 1:
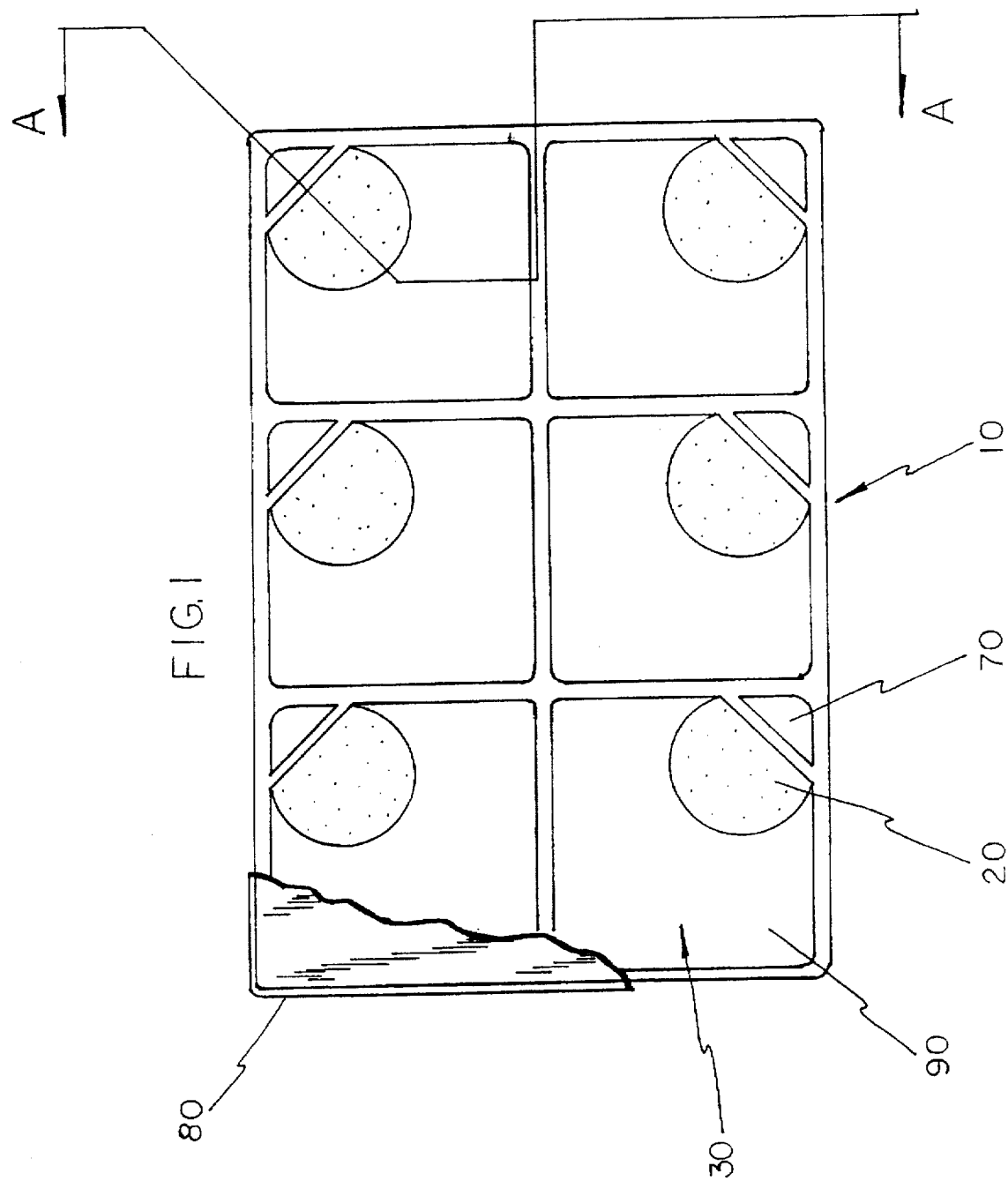
FIG. 1 is a top view of a compartmentalized multiple well tissue culture plate in accordance with the present invention.

REFERENCE NUMERALS IN DRAWINGS 10 compartmentalized multiple well tissue culture plate
20 membrane
30 basal medium compartment
40 cell culture compartment
50 culture medium
60 basal medium
70 cell culture compartment access port
80 top cover
90 basal medium access port
100 basal medium access port cap
110 membrane support
120 gas permeable film
130 gas film support
140 gas access opening
150 feet
170 basal medium head space 190 gas access channel
200 gas access channel cover
210 drain port
220 variable oxygen control compartment
230 lower gas permeable film
240 oxygen control compartment bottom
250 oxygen control compartment access port
260 liquid resistor
270 upper membrane support

DETAILED DESCRIPTION

Figure 2:
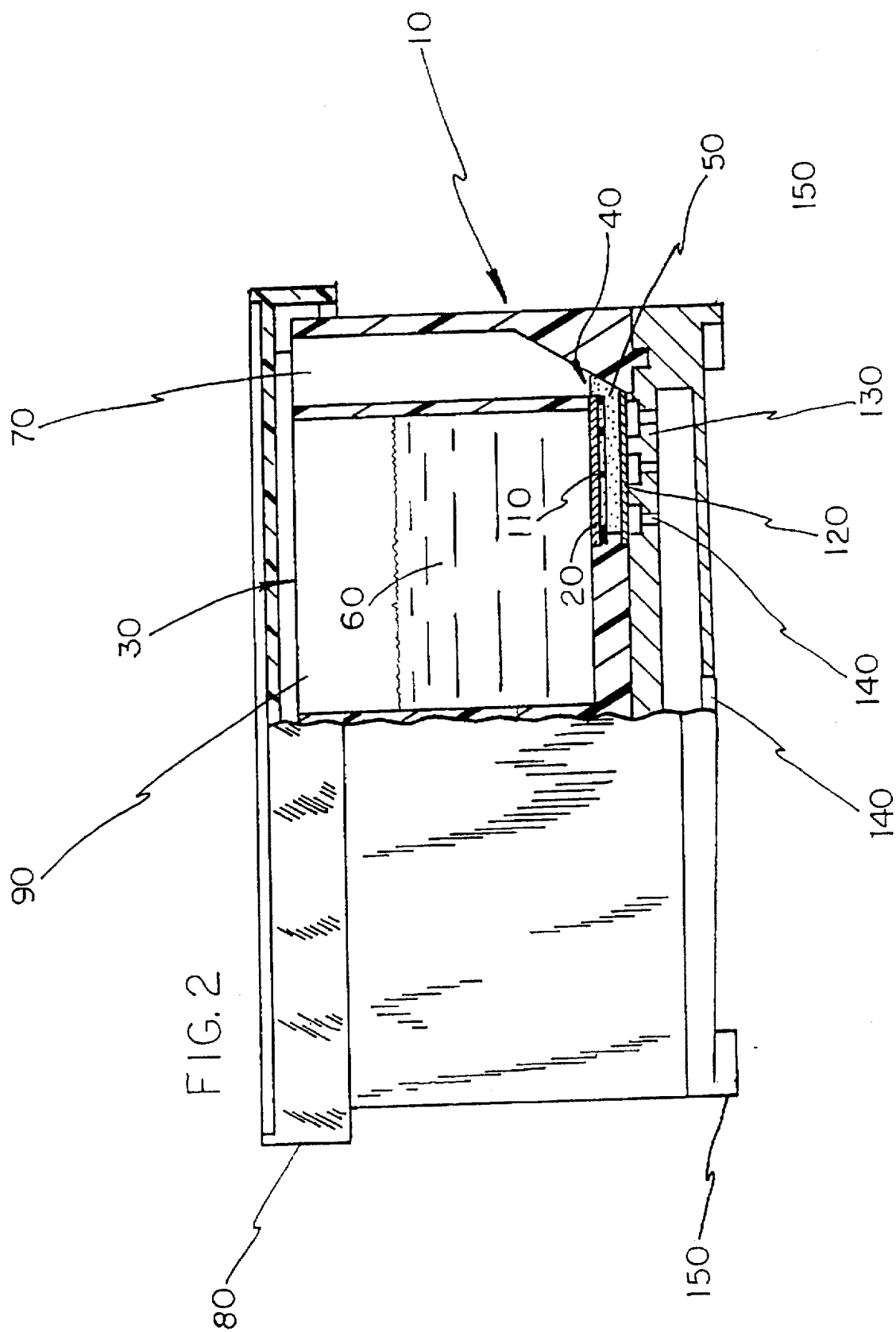
FIG. 2 is a partial cross-section taken through section A—A of the multiple well tissue culture plate of FIG. 1.

Referring now more specifically to the drawings, FIG. 1 shows a top view of a compartmentalized multiple well tissue culture plate 10 that housed six wells. FIG. 2 shows cross-sectional view A—A of FIG. 1. A membrane 20 separates each well of compartmentalized multiple well tissue culture plate 10 into a basal medium compartment 30 and a cell culture compartment 40. A culture medium 50 containing cells or tissue resides in cell culture compartment 40. A basal medium 60 resides in basal medium compartment 30. Access to cell culture compartment 40 is provided by a cell culture compartment access port 70. Access to basal medium compartment 30 is provided by a basal medium access port 90. A top cover 80 resides on top of compartmentalized multiple well tissue culture plate 10. Top cover 80 prevents contaminants from entering basal medium compartment 30 or cell culture compartment access port 70. Top cover 80 is configured to allow gases to move to and from basal medium 60. A membrane support 110 stabilizes membrane 20. A gas permeable film 120 resides on top of a gas film support 130 which is adapted to allow gas to contact the vast majority of the surface of gas permeable film 120 by way of gas access openings 140. Feet 150 lift gas film support 130 above the surface on which compartmentalized multiple well tissue culture plate 10 resides.

In operation, culture medium 50 containing cells or tissue of interest is introduced into cell culture compartment 40 through cell culture compartment access port 70 until it makes complete contact with the underside of membrane 20. Basal medium 60 is introduced into basal medium compartment 30 and a top cover 80 is placed upon compartmentalized tissue culture plate 10. The gas carrying capacity of the liquid medium is lowered when it experiences a temperature increase. Gas bubbles that may be released by culture medium 50 can be moved to cell culture compartment access port 70 by temporarily tilting compartmentalized multiple well tissue culture plate 10. This prevents gas from becoming trapped against the bottom of membrane 20 and limiting dialysis.

Membrane 20 is a material selectively permeable to a class of molecules. Several types of material are acceptable including cellulose, polyacrylonitrile, polysulfone, polycarbonate, and polyacrylamide. For example, dialysis membranes retaining molecules and compounds with molecular weights greater than 15,000 are commonly used to culture murine hybridoma cells. By using a membrane with this characteristic, cells, growth factors, and secreted antibodies are retained in cell culture compartment 40. In other applications, it may be advantageous to allow larger molecules and compounds to pass freely between basal medium 60 and culture medium 50. For example, high density culture of lymphocytes may require a large quantity of growth stimulating factors to be present. These factors, such as interleukin 2, can be introduced into basal medium 60 and culture medium 50. By appropriately selecting the pore size of membrane 20, a large source of these factors can be made available to the lymphocytes.

Membrane 20 will not exceed a molecular weight cutoff of 150,000 Daltons in most applications. Yet, there are applications where even larger pore sizes may be desirable. For example, if the purpose is only to culture a large number of cells, any pore size which retains the cells in cell culture compartment 40 can be used. In this case, a 0.2 uM or 0.45 uM microporous polycarbonate membrane such as that commercially available from Poretics Corporation (Livermore, Calif.) could be used.

Membrane support 110 stabilizes membrane 20. As basal medium 60 is added to basal medium compartment 30, the weight is transferred to membrane 20. Membrane support 110 keeps membrane 20 from sagging and displacing culture medium 50 into cell culture compartment access port 70. Membrane support 110 makes minimal contact with membrane 50 so the surface area for dialysis is not substantially diminished. Membrane support 110 is designed such that it will allow gas bubbles to move freely to cell culture compartment access port 70. Membrane support 110 can be made of any biocompatible material. In a preferred embodiment it is clear plastic such as polystyrene or polycarbonate. If membrane 20 is a material cast onto a stiff mesh backing or precise control of the volume of culture medium 50 residing above gas permeable film 120 is not required, membrane support 110 is optional.

Gas permeable film 120 is a biocompatible material capable of allowing transfer of gas into and out of cell culture compartment 40. Gas permeable film 120 can be either liquid permeable or impermeable, hydrophobic or hydrophilic, porous or non porous. Thickness can range above or below 0.25 mm. The best choice depends on the specific application. As a general guideline, the gas permeability of a given membrane should be considered in addition to the interaction of the membrane with either cells or protein structures. Liquid impermeable films of equivalent thickness will establish various steady state oxygen tension at the cell/gas permeable film interface. Fluorinated ethylene polymers, silicone, and silicone polycarbonate copolymers will establish higher oxygen tension than polyethylene, polycarbonate, polypropylene, polysulfone, or polypropylene polymers of equivalent thickness. In applications where protein denaturization, non-specific protein binding, cell membrane damage, or cell attachment is affected by the surface chemistry of the film, hydrophilic surfaces are more suitable. In applications where it is desirable to maintain the entire cell membrane in contact with water, hydrated gels may be most suitable.

The use of certain materials not normally associated with gas exchange can expand the options available for controlling oxygen tension at the cell/gas permeable film interface. For example, non-porous cellulose acetate has a relatively low oxygen gas permeability on the order of $7.3 \times 10^{-9}$ $cm^3 \cdot cm/(sec \cdot cm^2 \cdot atm)$. When cellulose acetate is made porous, it will increase oxygen permeability as it absorbs culture medium 50 with an oxygen permeability of $1.4 \times 10^{-6}$ $cm^3 \cdot cm/(sec \cdot cm^2 \cdot atm)$. In this manner, varying oxygen tension at the cell/gas permeable film interface of cell culture compartment 40 can be achieved by controlling the amount of culture medium 50 present in gas permeable film 120. Thus, oxygen tension variations will result by varying either the pore size, porosity, or tortuosity of gas permeable film 120.

Gas film support 130 holds gas permeable film 120 in a substantially horizontal position and stabilizes gas permeable film 120 to prevent sagging. Care should be given to assure the flatness of the gas permeable film is such that cells do not roll into or otherwise collect in low points. This is an undesirable event as the piling up of cells will create diffusional limitations and lead to cell death. On the other hand, care must also be taken to assure that gas exchange remains adequate. Thus, the desired amount of contact gas film support 130 makes with gas permeable film 120 will depend on the stiffness and gas permeability of gas permeable film 120 as well as gas exchange and metabolic requirements of a particular cell culture application. Most cell lines will become diffusionally limited at about ten to fifteen cell layers.

Gas film support 130 also acts to protect gas permeable film 120 from contamination or puncture. Minimal contact with gas permeable film 120 is made to allow the maximum possible surface area for gas transfer. Gas access opening 140 is located at the lowest point of gas film support 130 to allow condensation to exit gas film support 130. It is sized to allow adequate gas exchange of cell culture compartment 40 while minimizing evaporation. Gas film support 130 can be made of any structurally stable material, but in the preferred embodiment is an optically clear material such as polystyrene or polycarbonate to allow visual inspection of the culture. Feet 150 elevate tissue culture plate 10 such that gas film support 130 does not become scratched or visually impaired.

Figure 3:
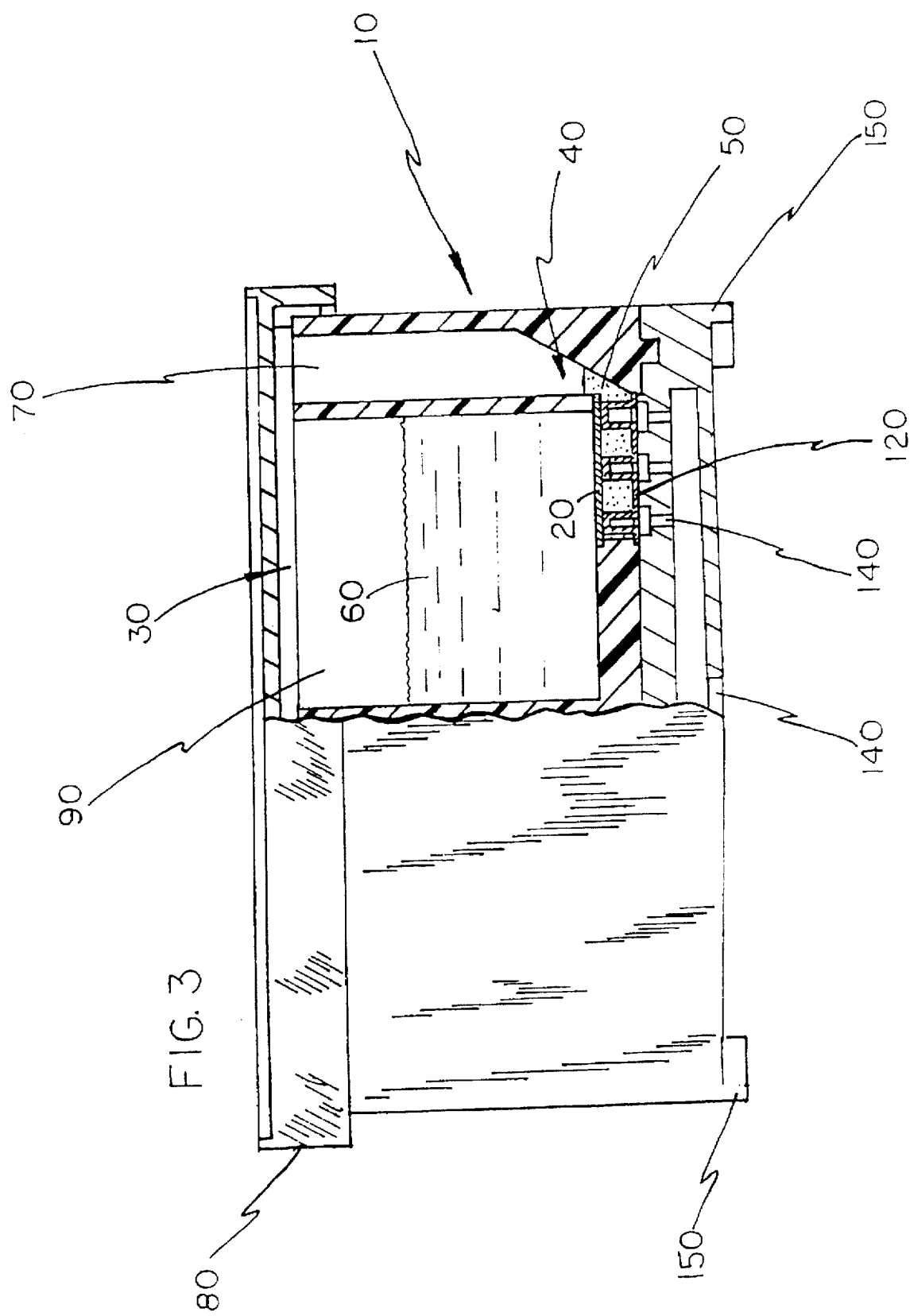
FIG. 3 is a cross-sectional view of a compartmentalized multiple well tissue culture plate showing an embodiment using a gas permeable membrane, portions of which project into the cell culture compartment.

The embodiment of FIG. 3 shows a configuration where portions of gas permeable film 120 project into cell culture compartment 40 to provide support of membrane 20 without the need for membrane support 110. Silicone is a good choice for material as it can be readily molded to form an appropriate shape. Wall thickness can be minimized to allow additional gas transfer into cell culture compartment 40. In the case of silicone, average wall thickness should be kept below 0.015 inches, preferably between 0.004 and 0.012 inches.

Figure 4:
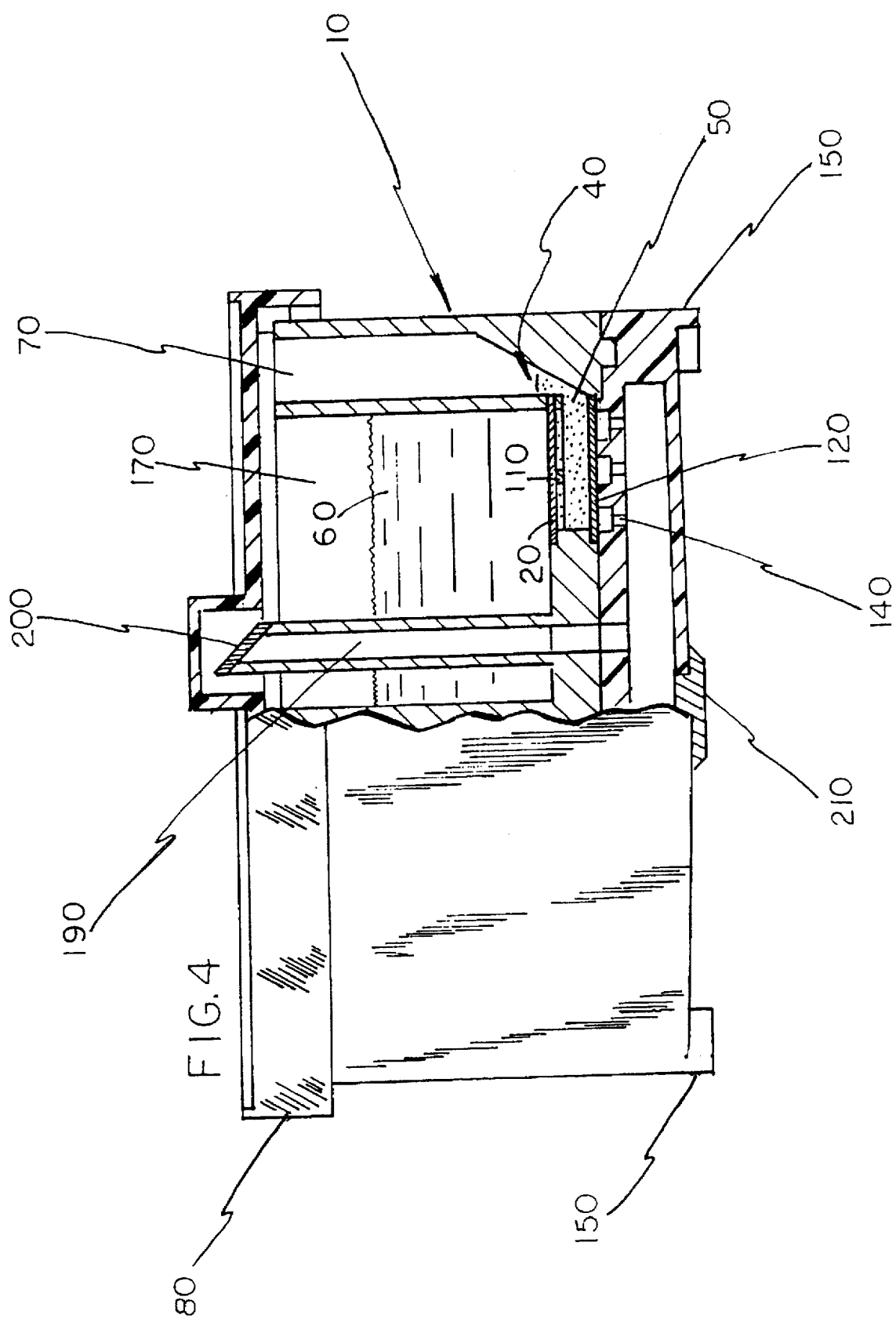
FIG. 4 is a cross-sectional view of a compartmentalized multiple well tissue culture plate showing an embodiment that controls evaporation.

Another consideration with regard to material selection for gas permeable film 120 is the moisture vapor transmission rate. Culture medium 50 will evaporate at various rates depending upon the material of gas permeable film 120. Limiting the cross-sectional area of gas access opening 140 can reduce the rate of evaporation, although the rate of liquid loss will also be a function of the ambient humidity which is more difficult to control. The embodiment of FIG. 4 addresses this issue.

Gas residing between basal medium 60 and top cover 80 is humidified by basal medium 60. The gas is placed in communication with the underside of gas permeable film 120 by a gas access channel 190. A gas access channel cover 200 is optional. It will prevent basal medium 60 from entering gas access channel 190 and limiting gas transfer. Gas access channel cover 200 is a gas permeable, liquid impermeable film. To prevent condensation from accumulating upon gas access channel cover 200 and diminishing gas transfer, it is not in a horizontal position. Thus, condensation can return to basal medium 60 by gravitational force. If used in embodiments in which individual basal medium wells are present, gas access channel 190 can remain uncovered. Gas access channel 190 is capable of collecting condensation in a drain port 210.

Many other methods of placing basal medium head space 170 in communication with gas permeable film 120 are possible. Care should be given to prevent condensation or basal medium 60 from diminishing gas transfer when gas access channel cover 200 is used.

Figure 5:
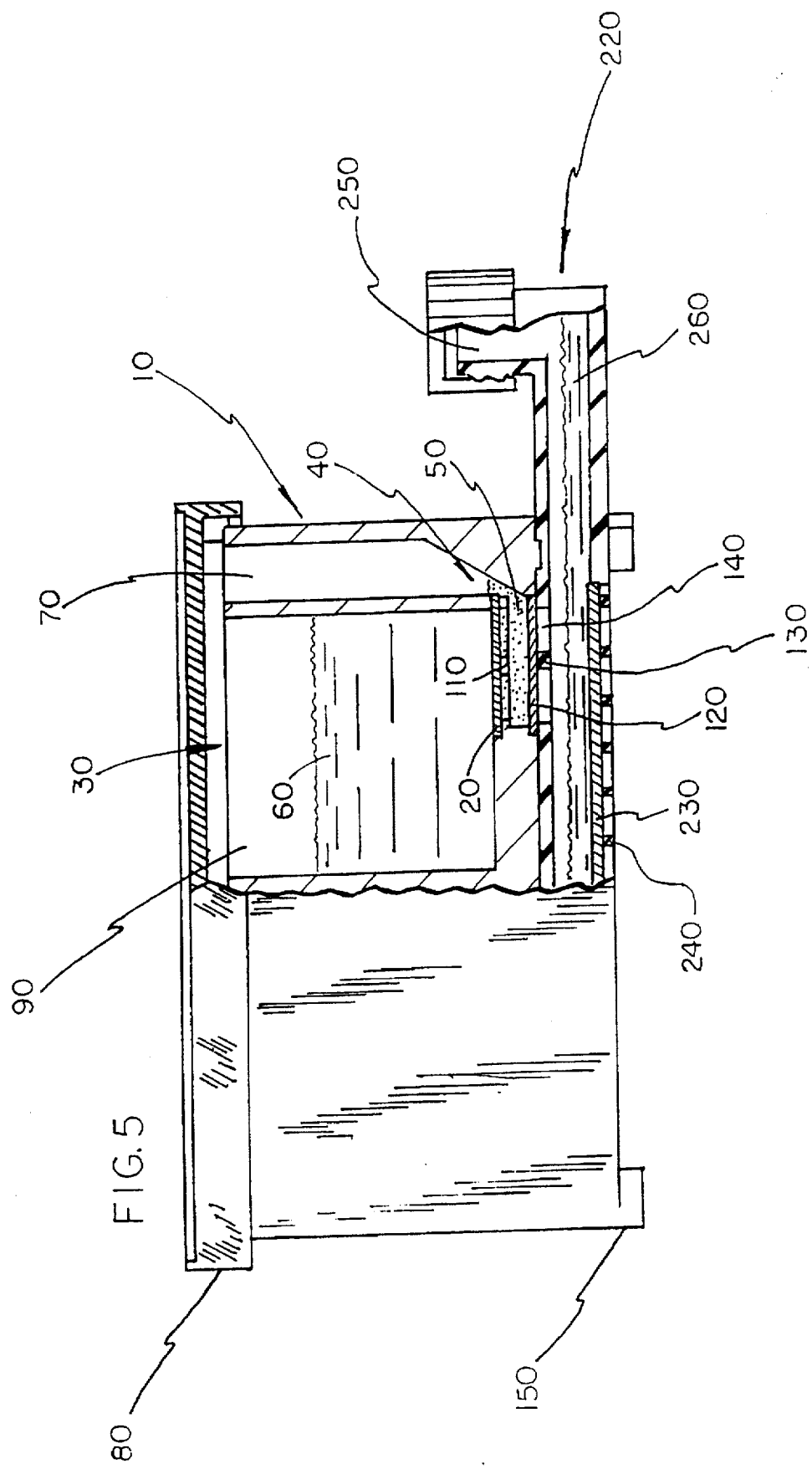
FIG. 5 is a cross-sectional view of a compartmentalized multiple well tissue culture plate showing an embodiment that allows variable oxygen tension.

If the type of materials available for gas permeable film 120 do not provide the desired oxygen tension, the configuration shown in FIG. 5 can be utilized. A variable oxygen control compartment 220 is composed of a lower gas permeable film 230 supported in a horizontal position by an oxygen control compartment bottom 240. An oxygen control compartment access port 250 allows a liquid resistor 260 to be introduced into variable oxygen control compartment 220. The oxygen tension at the bottom of gas permeable film 120 can be carefully controlled by varying the height of liquid residing upon a lower gas permeable film 230 in accordance with Fick's Law. Thus, liquid resistor 260 is any liquid used to diminish the mass transfer rate of oxygen from the ambient surroundings to the cells. Lower gas permeable film 230 can be any highly gas permeable film or sheet. In a preferred embodiment, it is liquid impermeable. Oxygen control compartment bottom 240 allows the vast majority of lower gas permeable film 230 to be in communication with the ambient environment. A hermetic seal exists between lower gas permeable film 230 and oxygen control compartment bottom 240. This seal can be made by welding, adhesives, or any other suitable method. The distance between the top of lower gas permeable film 230 and the bottom of gas permeable film 120 will preferably be from about 5 to 20 mm.

To minimize evaporation of liquid residing in variable oxygen control compartment 220, the underside of lower gas permeable film 230 can be placed in gaseous communication with basal medium head space 170 as previously described. Alternatively, ambient gas access can be minimized as described previously.

Figure 6:
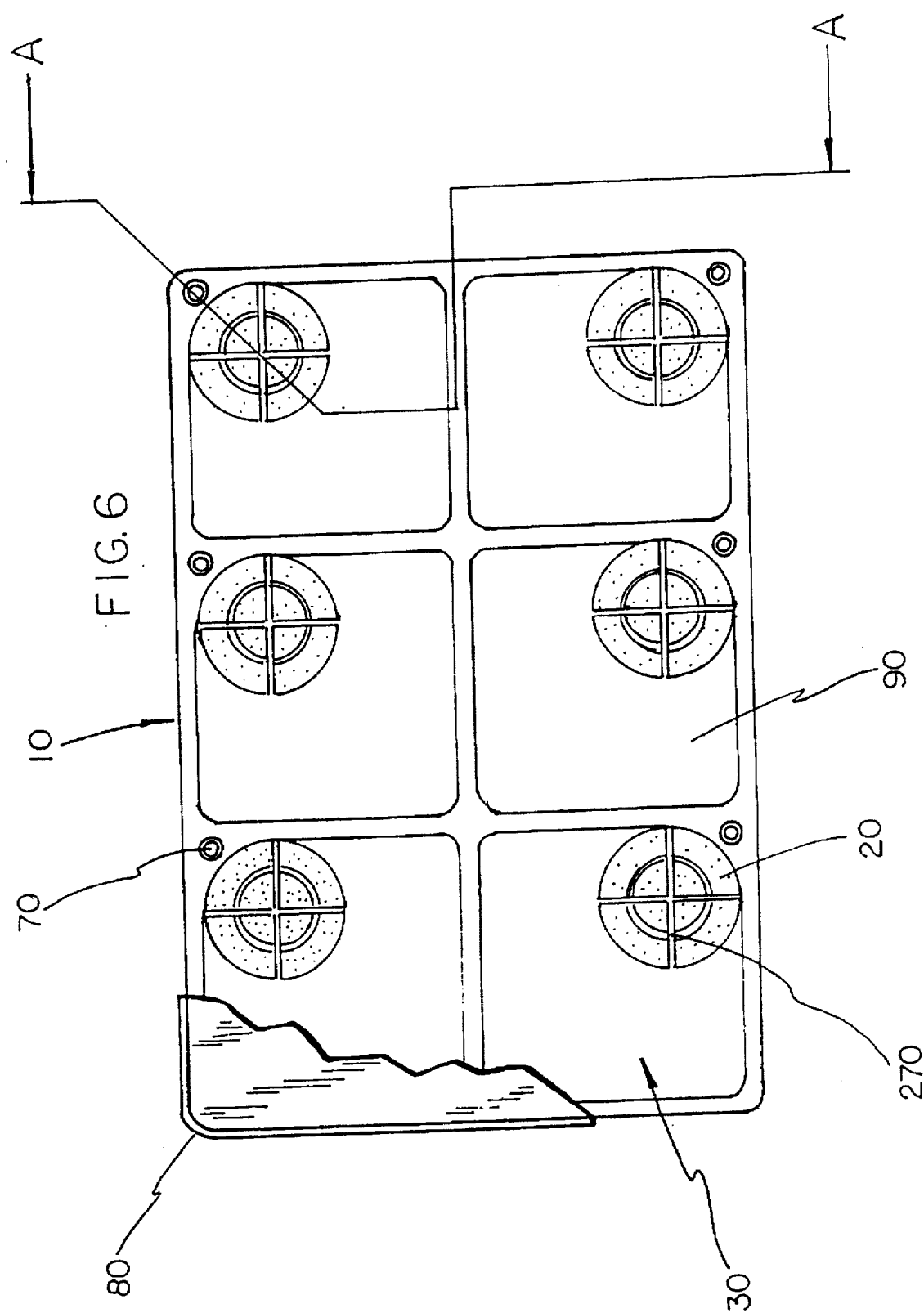
FIG. 6 is a top view of a compartmentalized multiple well tissue culture plate that balances hydrostatic pressure in two compartments.
Figure 7:
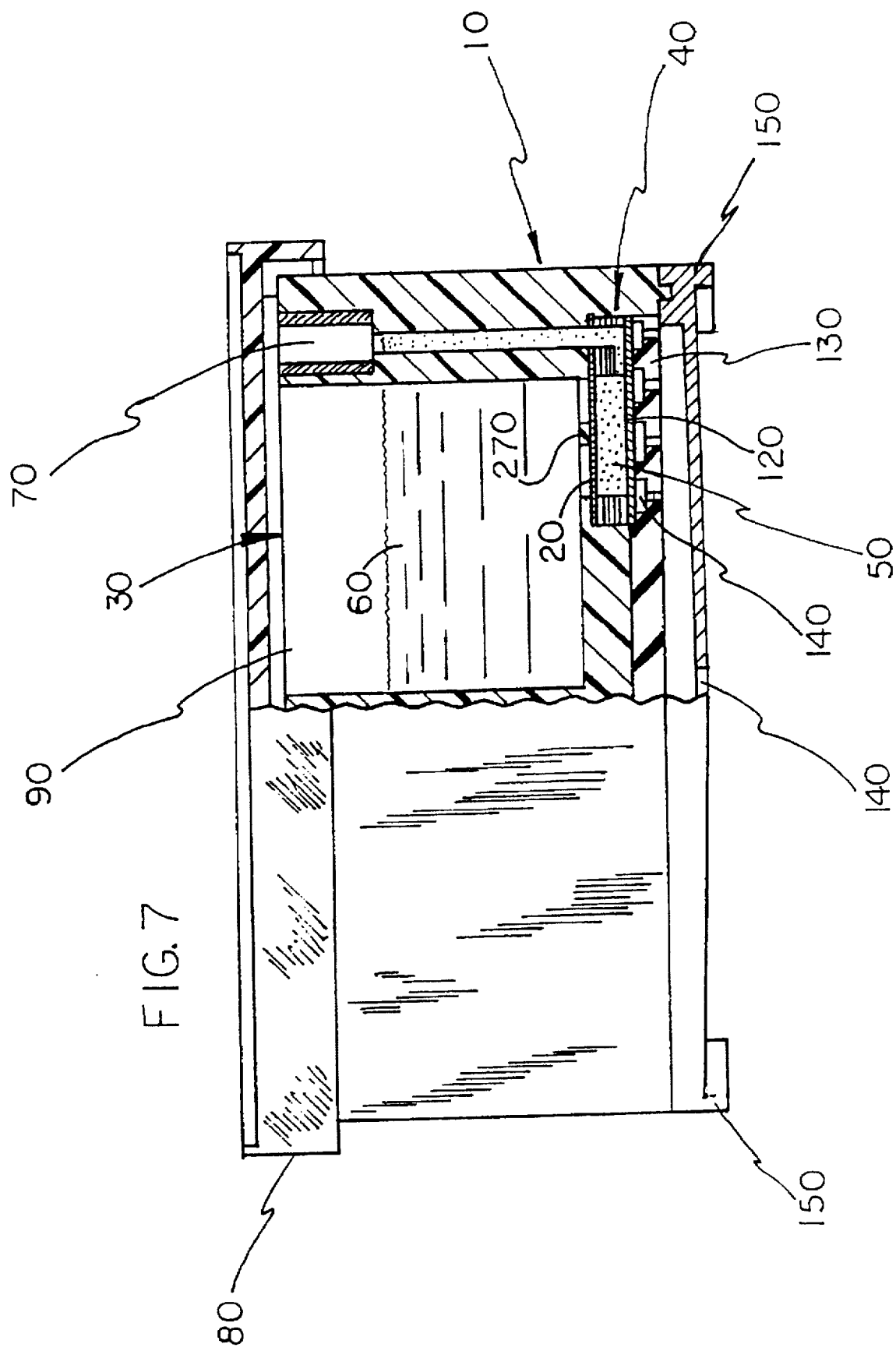
FIG. 7 is a partial cross-sectional view taken through section A—A of FIG. 6.

The embodiment shown in FIG. 6 and FIG. 7 keeps membrane 20 from sagging and insures liquid maintains contact with the upper and lower surface of membrane 20 during operation. It is particularly useful for applications in which a high concentration of cells is desired. Membrane support 110 is not present and this allows a very small volume of culture medium 50 to be used as well as preventing obstacles to cell removal. This embodiment is also capable of functioning with various volumes of culture medium 50, as liquid contact with membrane 20 is always assured.

In operation, as best shown in FIG. 7, membrane 20 is pressed onto the surface of gas permeable film 120 by the weight of basal medium 60. Putting the membrane in this position can also be achieved by generating a vacuum on cell culture compartment 40. A predetermined volume of culture medium 50 containing the desired culture is then introduced into cell culture compartment 40 by way of cell culture compartment access port 70. Culture medium 50 will come to rest within cell culture compartment access port 70 at a level that counterbalances the hydrostatic pressure of basal medium 60.

In the preferred embodiment, the volume of culture medium 50 residing in cell culture compartment access port 70 will be a small fraction of the volume of culture medium 50 residing between membrane 20 and gas permeable film 120. It is possible for water from basal medium 50 to move into cell culture compartment 40 if sufficient osmotic gradients develop across membrane 20. This condition can be remedied by configuring cell culture compartment access port 70 with excess capacity at a point higher than basal medium 60 will reside. Then liquid can collect in cell culture compartment access port 70, preventing an overflow condition.

Introducing culture medium 50 into cell culture compartment 40 will require enough pressure to overcome the hydrostatic pressure of basal medium 60. This can be accomplished by configuring cell culture compartment access port 70 to form a hermetic seal with a pipette, syringe, or some other culture medium container such as a bag or bottle. Culture medium 50 can be removed in the same manner.

This method of introducing culture medium 50 into cell culture compartment 40 and removing it therefrom can be utilized in all of the embodiments described herein. In most embodiments using membrane support 110, it will be necessary to provide a vent to allow air access to and from cell culture compartment 40. The vent is required to allow gas to be displaced when culture medium 50 is introduced into culture compartment 40. The vent also allows gas to displace culture medium 50 when it is removed from cell culture compartment 40. Cell culture compartment access port 70 can be designed to allow gas to move in and out while culture medium 50 is added and removed. Thus, cell culture compartment 40 can be effectively vented using only one cell culture compartment access port 70.

The embodiment of FIG. 7 does not require a vent. When membrane 20 is pressed against gas permeable film 120, air is displaced from cell culture compartment 40 prior to introducing culture medium 50. When culture medium 50 is removed, membrane 20 is simply lowered. Thus, there is never the need for gas and liquid to move to and from cell culture compartment 40 simultaneously. Gas bubbles that may accumulate in cell culture compartment 40 can be removed by tilting the device, inserting a pipette into cell culture compartment access port 70 and drawing the gas bubbles out. Cell culture compartment access port 70 should be formed of a biocompatible material soft enough to seal the pipette. Silicone of 70 Shore A durometer is suitable.

When the embodiment shown in FIG. 7 is used for high density culture, the average distance between membrane 20 and gas permeable film 120 should be less than about 5 millimeters, preferably about 1 mm to 2 mm.

The embodiment of FIG. 7 can also be used to prevent evaporation of culture medium 50 from allowing membrane 20 to lose contact with culture medium 50. Membrane 20 is essentially floating on culture medium 50 and as culture medium 50 evaporates through gas permeable film 120, membrane 20 simply gets closer to gas permeable film 120. No dialysis limitation occurs as membrane 20 is always in contact with culture medium 50.

In cases where membrane 20 is comprised of material such as cellulose that swells or becomes baggy when wet, it may be desirable to constrain membrane 20 with an upper membrane support 270. Upper membrane support 270 stops upward travel of membrane 20 as culture medium 50 enters cell culture compartment 40. Culture medium 50 presses membrane 20 against upper membrane support 270, smoothing wrinkles.

Wrinkles in membrane 20 can lead to an uneven distribution of cells during inoculation. If membrane 20 were severely wrinkled, culture medium 50 would reside within the wrinkles. Then some areas above gas permeable film 120 would have more culture medium 50 residing above it than others. Cell in the inoculum are distributed equally throughout culture medium 50. Eventually, these cells settle onto gas permeable film 120. Areas of gas permeable film 120 in which a larger volume of culture medium 50 resides above it will receive more cells. Therefore, the wrinkling of membrane 20 should be minimized.

Upper membrane support 270 can be biocompatible material such as virgin grade polystyrene or polypropylene. Care should be given to insure that it does not limit dialysis. In the preferred embodiment, it should be about 70% to 90% open Although there is no restriction on either the shape or size of cell culture compartment 40, the advantageous distance between gas permeable film 120 and membrane 20 is about 1 to 5 millimeters to obtain a high concentration of cells and cell secreted products. When gas permeable film 120 is substantially flat and horizontal, up to about $30 \times 10^6$ cells per square centimeter of surface area can be expected to remain viable. These cells can pile up to a height of about 300 micrometers. Thus, membrane 20 is in no danger of contacting cells and becoming clogged when it is spaced at least about 1 mm from gas permeable film 120.

In order to minimize the frequency of basal medium 60 exchanges, the volume of basal medium 30 is sized relative to the surface area of gas permeable film 120. For suspension cells that reside in static culture at one million cells per milliliter, about 5 to 10 ml of basal medium 60 are required for every 1 $cm^2$ of gas permeable film 120. When culturing anchorage dependent cells growing in monolayer, advantageously the volume of basal medium 60 (milliliters) exceeds the surface area (square centimeters) of gas permeable film 120 by at least a factor of about two.

Factors that affect the amount of solute mass transfer into and out of cell culture compartment 40 include the surface area of membrane 20. As a general guideline, the surface area of membrane 20 should be approximately equal to the surface area of gas permeable film 120. In applications where only 1 to 2 million moderately metabolically active cells are to be supported per square centimeter of gas permeable film 120, the surface area of membrane 20 can be reduced to about ¼ to ½ of the surface area of gas permeable film 120.

Figure 8:
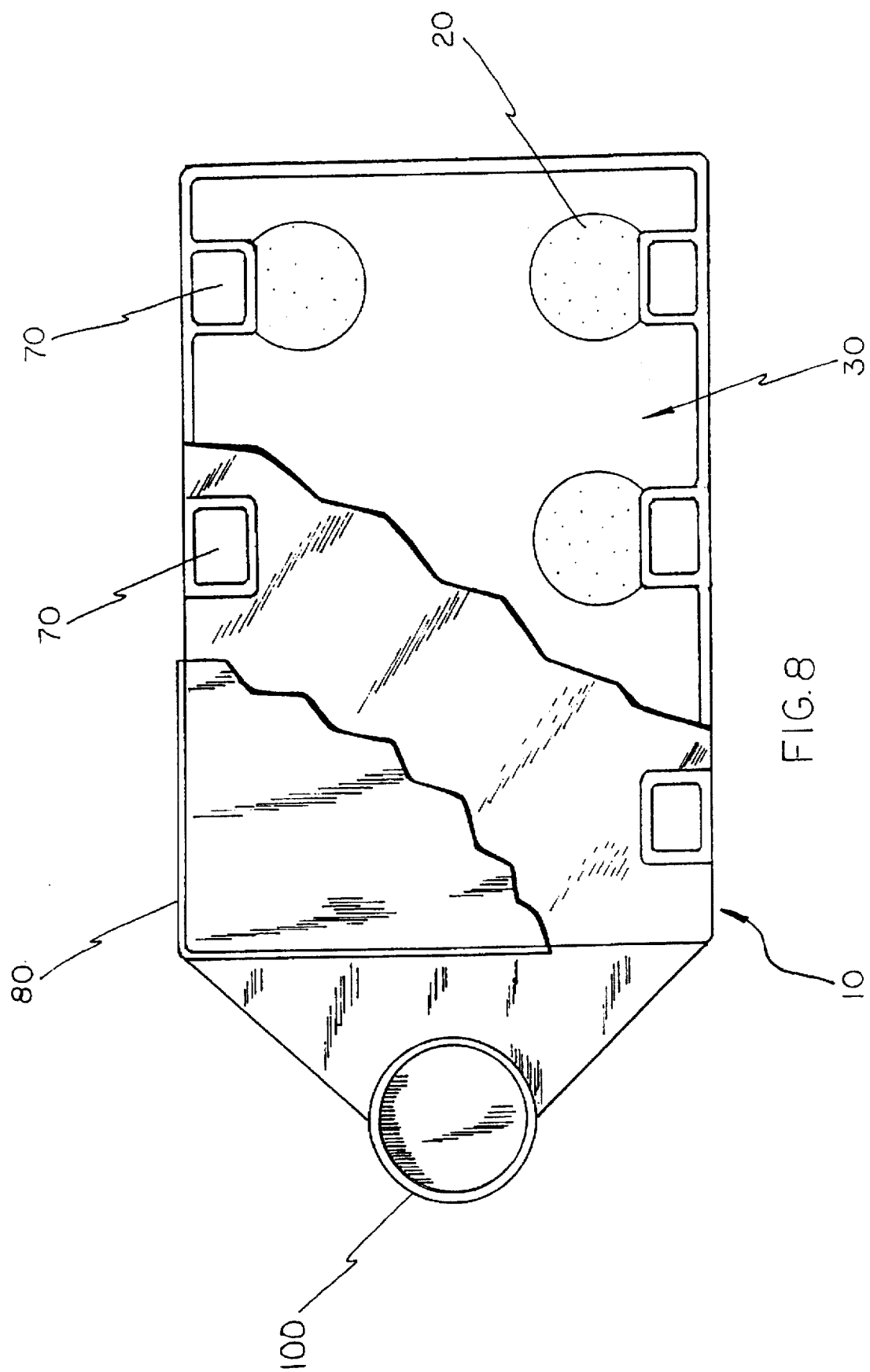
FIG. 8 is a top view of a compartmentalized tissue culture plate in which basal medium resides in a common reservoir.
Figure 9:
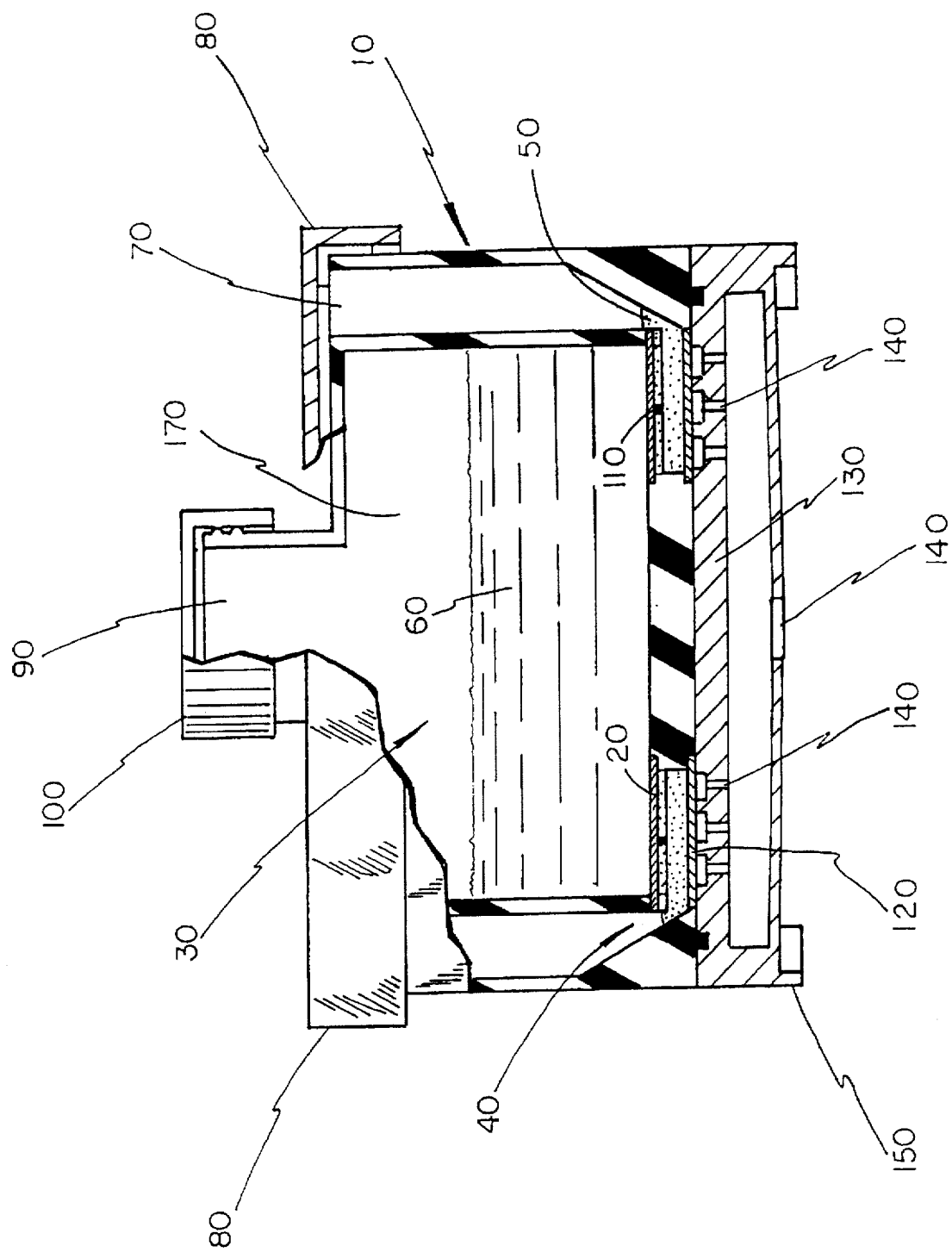
FIG. 9 is a cut away view of the compartmentalized multiple well tissue culture plate of FIG. 8.

In the embodiment shown in FIG. 8 and FIG. 9, basal medium 60 is introduced into basal medium compartment 30 through basal medium access port 90. Preferably, a basal medium head space 170 is maintained between basal medium 60 and the top of basal medium compartment 30, and basal medium access port cap is slightly loosened. This allows ambient gas to influence the pH of basal medium 60 and prevents pressurization of basal medium compartment 30. A basal medium access port cap of the type used in Falcon® multiple well tissue culture plates (commercially available from Becton Dickenson Labware—Plymouth, England) may be used in cases where the cap should remain tightened due to contamination concerns.

In all embodiments, the housing of compartmentalized multiple well tissue culture plate 10 can be any biocompatible material. It is preferable that the housing will provide optical clarity so the medium can be visually monitored for determining the pH of the medium or detecting possible microbial contamination. Polystyrene is a favored selection. Construction of compartmentalized multiple well tissue culture plate 10 can be by ultrasonic welding, mechanical fasteners, solvent bonding or any other method which provides leak proof integrity. Gas permeable film 120 and membrane 20 can be sealed by o-rings, gaskets, welding, adhesives, or any other method which provides leak proof integrity. In a preferred embodiment, all materials used in the compartmentalized multiple well tissue culture plate 10 are compatible with gamma sterilization.

Those skilled in the art will appreciate that numerous modifications can be made without departing from the spirit of the present invention. Therefore, it is not intended to limit the breadth of the invention to the embodiments illustrated and described. Rather, the scope of the invention is to be determined by the appended claims and their equivalents.

What is claimed is:

1. A static self contained cell culture device consisting essential of a container having:
   a) a plurality of cell culture compartments each including a gas permeable film (120) disposed below an upper sheet (20) selectivity permeable to compounds of less than a particular size, and a means of spacing said gas permeable film (120) from said upper sheet (20) so as to allow a culture medium (50) to reside between said upper sheet (20) and said gas permeable film (120);
   b) means defining a basal medium compartment (30) above said cell culture compartments (40) to allow a basal medium (60) to reside upon said upper sheet (20);
   c) an access port (70) to each of said cell culture compartments (40);
   d) an access port (90) to said basal medium compartment (30); and
   e) a gas film support (130) below and in partial contact with said gas permeable film (120) such that suspension cells can distribute across said gas permeable film (120) and gas transfer into and out of said cell culture compartment (40) is not substantially impaired.

2. A device according to claim 1, having at least two of said cell culture compartments (40) residing below a common basal medium compartment (30).

3. A device according to claim 1, wherein within each cell compartment (40) the surface area of said upper sheet (20) is at least one quarter of the surface area of said gas permeable film (120).

4. A device according to claim 1, wherein within each cell compartment (40) the average distance between the substantially horizontal portion of said gas permeable film (120) and said upper sheet (20) is less than 5 millimeters.

5. A device according to claim 1, wherein the smallest cross-sectional area of said gas film support (130) open to gaseous communication with the ambient environment is less than the total surface area of the underside of said gas permeable film (120) in contact with gas.

6. A device according to claim 1, including an upper sheet support (270) above said upper sheet (20).

7. A device according to claim 1, wherein said gas permeable film (120) includes sections which project into said cell culture compartments (40).

8. A device according to claim 1, including (f) means providing gaseous communication between the top of said basal medium compartment (30) and the underside of said gas permeable film (120).

9. A device according to claim 8, wherein said gas permeable film (120) includes sections which project into said cell culture compartments (40).

10. A device according to claim 8, having at least two of said cell culture compartments (40) residing below a common basal medium reservoir (30).

11. A device according to claim 10, wherein said gas permeable film (120) includes sections which project into said cell culture compartment (40).

12. A method of culturing cells in a cell culture device according to claim 1, comprising the steps of;
   a) positioning said device so that said gas permeable film (120) is in a substantially horizontal position;
   b) placing a basal medium (60) in said basal medium compartment (30) above said upper sheet (20) said basal medium (60) contacting said upper sheet (20);
   c) placing cells and a cell culture medium (50) in at least one cell culture compartment (40), said cell culture medium (50) communicating with said basal medium (60) by way of said upper sheet (20);
   d) maintaining said cells at a selected temperature; and
   e) allowing gas exchange through said gas permeable film (120), whereby cells are allowed to proliferate upon said upper surface of said gas permeable film (120).

13. A method according to claim 12, wherein said gas permeable film (120) includes sections which project into said cell culture compartment (40).

14. A static self contained cell culture device consisting essentially of a container having:
   (a) a plurality of cell culture compartments (40) each including a first gas permeable film (120) disposed below and an upper sheet (20) selectively permeable to compounds of less than a particular size, means separating said first gas permeable film (120) from said upper sheet (20) to allow a culture medium (50) to reside between said upper sheet (20) and said first gas permeable film (120);
   b) means defining a basal medium compartment (30) above said cell culture compartments (40) to allow a basal medium (60) to reside in contact with said upper sheet (20);
   c) an access port (70) to each of said cell culture compartments (40);
   d) an access port (90) to said basal medium compartment;
   e) a gas film support (130) below and in partial contact with said first gas permeable film (120) suspension cells can distribute across said gas permeable film (120) and gas transfer into and out of said cell culture compartment (40) is not substantially impaired;
   f) a second gas permeable film (230) disposed in a horizontal position below said first gas permeable film (120);
   g) separating means between said first gas permeable film (120) and said second gas permeable film (230) to form a variable oxygen control compartment (220) adapted to contain fluid; and
   h) an access port (250) to said variable oxygen control compartment (220) whereby liquid can be added or removed to control the rate of gas transport.

15. A device according to claim 14, wherein said first gas permeable film (120) includes sections which project into said cell culture compartment (40).

16. A device according to claim 14, at least two of said cell culture compartments (40) residing below a common said basal medium reservoir (30).

17. A device according to claim 16, wherein said first gas permeable film (120) includes sections which project into said cell culture compartment (40).

18. A method of culturing cells comprising the steps:
   a) forming a plurality of cell culture compartments (40) each of said cell culture compartments (40) comprising of a gas permeable film (120) disposed below an upper sheet (20) selectively permeable to compounds of less than a particular size;
   b) forming a gas film support (130) disposed below said gas permeable film (120) and adapted to hold said gas permeable film (120) in a substantially horizontal position while allowing gas to contact the underside of said gas permeable film (120);
   c) placing a basal medium (60) in a self contained basal medium compartment (30) above at least one cell culture compartment (40), said basal medium (60) communicating with cell culture medium (50) by way of said upper sheet (20) maintaining said basal medium in a substantially quiescent state;

d) placing cells and a cell culture medium (50) in at least one of said cell culture compartments (40), said cell culture medium (50) in communication with basal medium (60) by way of said upper sheet (20);

e) maintaining said cells at a selected temperature; and f) allowing gas exchange through said gas permeable film (120), whereby cells are allowed to proliferate upon the upper surface of said gas permeable film (120).

19. The method according to claim 18, wherein within each cell culture compartment (40) the average distance between said upper sheet (20) and the substantially horizontal-portion of said gas permeable film (120) does not exceed 15 millimeters.

20. A method of culturing cells comprising the steps:

a) forming a plurality of cell culture compartment (40), each of said cell culture compartments (40) comprising a gas permeable, liquid permeable film (120) disposed below an upper sheet (20) selectively permeable to compounds of less than a particular size;

b) placing a basal medium (60) in at least one compartment above a cell culture compartment (40), said basal medium (60) contacting with said upper sheet (20);

c) placing the cells and a cell culture medium (50) in at least one of said cell culture compartments (40), said cell culture medium (50) communicating with basal medium (60) by way of said upper sheet (20);

d) maintaining said cells at an appropriate temperature; and e) allowing gas to reside below said gas permeable, liquid permeable film (120).

21. A method of culturing cells comprising the steps;

a) forming a plurality of cell culture compartment (40), each of said cell culture compartments (40) comprising a first gas permeable film (120) disposed below an upper sheet (20) permeable to compounds of less than a particular size;

b) placing said cell culture compartment (40) upon a variable oxygen control compartment (220) comprised of a bottom second gas permeable film (230) disposed below an upper gas film support (130), maintaining said first gas permeable film (120) of said cell culture compartment (40) in a substantially horizontal position;

c) placing a basal medium (60) in a self contained basal medium compartment (30) above at least one of said cell culture compartment (30), said basal medium (60) contacting with said upper sheet (20);

d) placing cells and a cell culture medium (50) in said cell culture compartment (40), said cell culture medium (50) communicating with basal medium (60) by way of said upper sheet (20);

e) placing a selected volume of a liquid (260) into said variable oxygen control compartment (220);

f) maintaining said cells at a predetermined temperature; and g) allowing oxygen and carbon dioxide to diffuse through said gas permeable film (120) by way of said liquid (260) and said bottom second gas permeable film (230) of said variable oxygen control compartment (220), whereby cells are allowed to proliferate upon the upper surface of said first gas permeable film 120, and h) optionally varying the oxygen tension within said cell culture compartment 40 by adding or removing said liquid (260) from said variable oxygen control compartment (40).

22. A method of culturing cells comprising the steps of:

a) forming a plurality of cell culture compartment (40), each of said cell culture compartments (40) comprising a gas permeable film (120) disposed below an upper sheet (20) selectively permeable to compounds of less than a particular size;

b) forming an access port (70) to each of said formed cell culture compartments (40);

c) maintaining said gas permeable film (120) in a substantially horizontal position;

d) placing a basal medium (60) in a self contained basal medium compartment (40), said basal medium (60) contacting said upper sheet (20) maintaining said basal medium in a substantially quiescent state;

e) placing cells and a cell culture medium (50) in at least one of said cell culture compartments (40), said culture medium (50) communicating with said basal medium (60) by way of upper sheet (20);

f) allowing a pressure equilibrium to be established across said upper sheet (20) of said cell culture compartments (40) by allowing the liquid level in said culture compartment to rise into said access port of said cell culture compartment to counter balance the hydrostatic pressure of said basal medium;

g) maintaining said cells at a selected temperature; and h) allowing gas exchange through said gas permeable film (120) whereby cells are allowed to proliferate upon the upper surface of said gas permeable film (120).

23. A method according to claim 22, wherein;

a) the entrance of said access port (70) to said cell culture compartment (40) resides at a height at least equal to the upper surface of said basal medium (60).

24. A method according to claim 22, wherein said gas permeable film (120) includes sections which project into said cell culture compartment (40).

* * * * *

UNITED STATES PATENT AND TRADEMARK OFFICE
CERTIFICATE OF CORRECTION

PATENT NO. : 5,707,869
DATED : January 13, 1998
INVENTOR(S) : Wolf, et al.

It is certified that error appears in the above-indentified patent and that said Letters Patent is hereby corrected as shown below:

Title Page          After " [45] Date of Patent: Insert
                    -- * --

Title Page          Insert -- [*] Notice:
                    The term of this patent shall
                    not extend beyond the expirat-
                    ion date of Pat. No. 5,693,
                    537. --

Col. 12, claim 16   After " claim 14, " insert
line 1              -- having --

Signed and Sealed this

Fifteenth Day of May, 2001

Attest:

NICHOLAS P. GODICI

*Attesting Officer*          Acting Director of the United States Patent and Trademark Office